United States Patent

Rising et al.

[11] Patent Number: 5,146,794
[45] Date of Patent: Sep. 15, 1992

[54] FILTER PUNCH AND FILTER COLLECTION SYSTEM

[75] Inventors: Donald B. Rising, Stowe; Kenneth G. Desilets, Westford; Thomas Zermani, Concord, all of Mass.

[73] Assignee: Millipore Corporation, Bedford, Mass.

[21] Appl. No.: 731,574

[22] Filed: Jul. 17, 1991

Related U.S. Application Data

[60] Continuation-in-part of Ser. No. 583,428, Oct. 15, 1990, Pat. No. 5,062,308, which is a division of Ser. No. 169,523, Mar. 17, 1988, Pat. No. 4,974,462.

[51] Int. Cl.$^5$ .............................................. G01N 1/04
[52] U.S. Cl. .................................................. 73/864.41
[58] Field of Search ......................... 73/863.23, 864.41; 30/366, 367; 210/85; 55/270; 422/68, 99, 101

[56] References Cited

U.S. PATENT DOCUMENTS

| | | | |
|---|---|---|---|
| 2,013,758 | 9/1935 | Livermore | 30/366 |
| 2,145,725 | 1/1939 | Jamieson | 30/366 |
| 4,250,899 | 2/1981 | Pagani | 131/254 |
| 4,277,249 | 7/1981 | Broughton | 435/7 |
| 4,629,236 | 12/1986 | Smith | 294/61 |
| 4,807,367 | 2/1989 | Loerwald | 30/367 |
| 4,848,309 | 7/1989 | Alderete | 30/367 |
| 4,969,269 | 11/1990 | Dominguez | 30/366 |

*Primary Examiner*—Robert Raevis
*Attorney, Agent, or Firm*—Andrew T. Karnakis; Paul J. Cook

[57] ABSTRACT

A filter punch construction is provided for use in conjunction with a multiwell filtration device wherein each well includes a filtration membrane. The punch has a leading surface to which is secured an elongated piercing member having a sharp point and a periphery comprising holding or cutting edges and a following surface which has a guide member. The piercing member and cutting edges pierce the filtration membrane in each well and push the entire filter and retentate thereon into a receptacle vial.

11 Claims, 2 Drawing Sheets

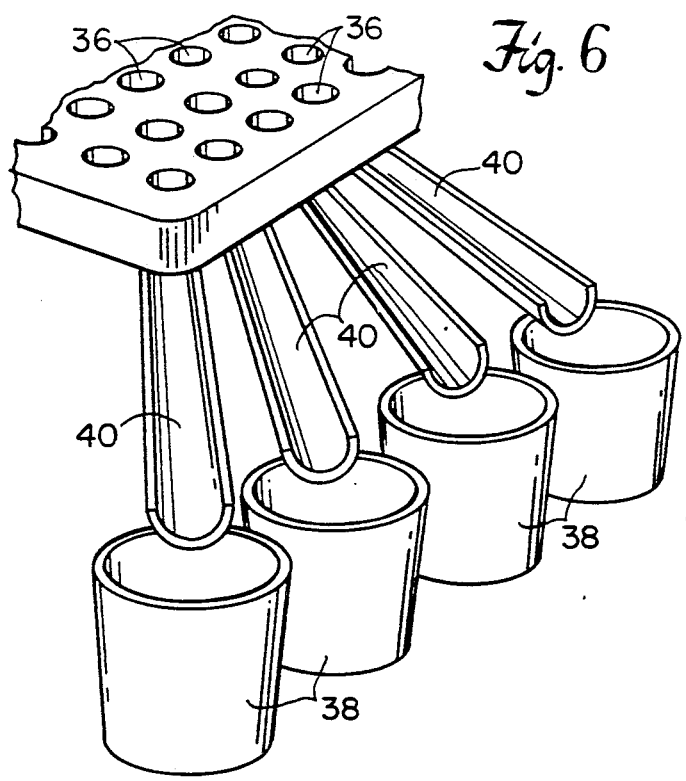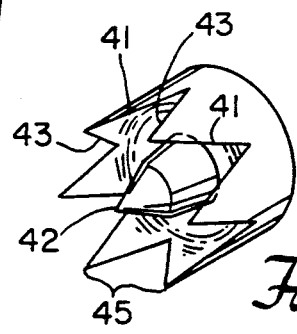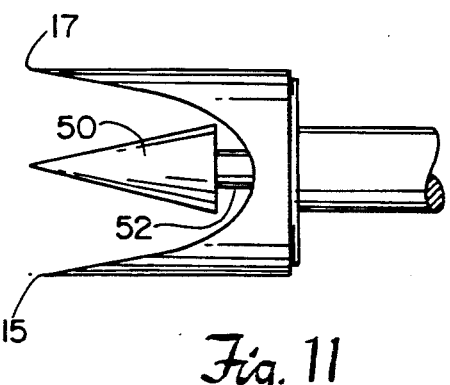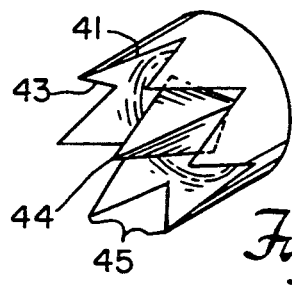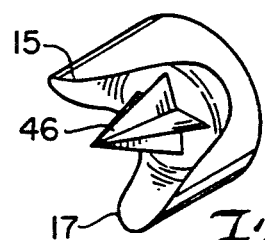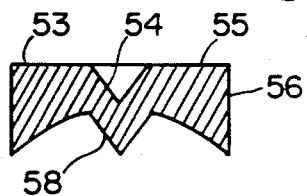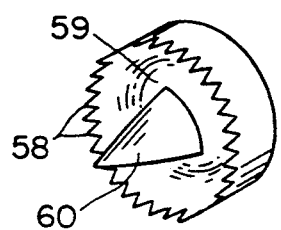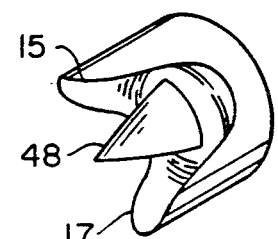

FILTER PUNCH AND FILTER COLLECTION SYSTEM

REFERENCE TO RELATED APPLICATIONS

This application is a continuation in part of copending application Ser. No. 583,428, filed Oct. 15, 1990, now U.S. Pat. No. 5,062,308, which in turn, is a divisional application of application Ser. No. 169,523, filed Mar. 17, 1988, now U.S. Pat. No. 4,974,462.

BACKGROUND OF THE INVENTION

This invention relates to a filter punch construction and to a system utilizing the filter punch for collecting sample deposited on a filter.

Test plates for in vitro analysis which contain a multiplicity of individual wells or reaction chambers are commonly known laboratory tools. Such devices have been employed for a wide variety of purposes and assays as exemplified by U.S. Pat. Nos. 3,694,464; 4,304,865; 4,276,048; 4,154,795; 4,427,415; 4,526,690 and Re 30,562. Microporous membrane filters and filtration devices containing such microporous membranes have been especially useful with many of the recently developed cell and tissue culture techniques and assays, particularly those in the field of virology and immunology, wherein the material of interest is retained by the filter. Typically, a ninety-six well filtration plate is used to conduct multiple assays simultaneously, some steps of which last several hours prior to performing filtration. Subsequent to filtration, it is common practice to utilize a die-punch having a flat face which is inserted into the well and through the filter paper bearing the retentate in order to direct the filter paper and retentate from the well into a vial for subsequent testing. This system has two major problems. First, many times only a portion of the filter paper circumference is sheared and the filter disc remains attached to the well. Secondly, the flat face of the punch tends to remove some of the retentate from the filter paper so that the subsequent testing is inaccurate. An alternative system utilizes a hollow tube as a punch to minimize the contact face of the punch and reduce the amount of sample accidentally transferred to the punch. In another system, the filter is scored about its circumference in order to facilitate subsequent punching. This system is undesirable since accidental rupturing of the filter paper along the scoring can occur during filtration.

The filter punch disclosed in U.S. Pat. No. 4,974,462, while a great improvement over previous punching means, does not provide 100% complete filter removal with fragile membranes. This is because the filter periphery does not separate everywhere simultaneously. Sometimes, the unbroken portion of the periphery imposes a side force upon the filter section. These side forces can cause a fragile filter material to tear away from the central piercing point, with the result that the filter disk remains attached to the well at a portion of the disk periphery.

A probe tip apparatus for removing liquid from a sealed vial is disclosed in U.S. Pat. No. 4,862,753. The probe tip includes exposed cutting surfaces for cutting a seal on the vial and a probe centrally located within the cutting edges for removing liquid from the vial by suction.

Accordingly, it would be desirable to provide a means for removing retentate and filter paper from a multi-well filtration plate which assures that the filter paper will be completely removed from the well without loss of a portion of the retentate for purposes of subsequent testing. Furthermore, it would be desirable to provide such a means which permits removal of the filter and retentate from a plurality of wells simultaneously.

SUMMARY OF THE INVENTION

The present invention provides a filter punch and filter punch system which can be utilized in conjunction with a multi-well filtration plate in order to remove retentate and filter from each well subsequent to a filtration step which utilizes the multi-well filtration plate. The filter punch includes an elongated piercing member having a sharp point on a central portion of a lead surface of the punch and a guide element from a following surface of the punch. The lead surface also has sharp peripheral points which extend in the same general direction as the centrally located piercing point. The peripheral points initiate cutting of the filter disk at multiple locations and then help to prevent relative sideways motion of the filter section. The central piercing point acts in concert with the peripheral points to prevent sideways movement of the filter section relative to the cutting edge, and also secures the cut filter to the punch for transfer into a receptacle vial. In a preferred embodiment, two peripheral points pierce and begin cutting the filter periphery. The central piercing member then pierces the filter as peripheral cutting continues. The central piercing member can be shorter than, longer than or the same length as the peripheral points so long as this function is effected. The piercing point is positioned to pierce the central portion of the filter in the well while the guide protrusion is positioned to permit a suitably shaped driving member to push the punch through the filter. The secondary points are incorporated as part of the lead surface periphery of the punch. The periphery of the lead surface then forces essentially the entire filtration area to separate from the filter material surrounding the filtration area. The filter and retentate thereon are directed to a receptacle wherein the retentate can be tested. There is no loss of retentate since the filter punch accompanies the filter with all of the retentate positioned between the filter and the punch lead surface. In another aspect of this invention, a filter punch holder is provided for retaining rows of punches in a manner so that a plurality of filter punches can be utilized simultaneously to remove retentate and filter from a plurality of wells.

BRIEF DESCRIPTION OF THE DRAWINGS

FIG. 6 illustrates the use of the filter punch and filter punch holder of this invention.

FIG. 7 illustrates an alternative embodiment of this invention.

FIG. 8 illustrates an alternative embodiment of this invention.

FIG. 9 illustrates an alternative embodiment of this invention.

FIG. 10 illustrates an alternative embodiment of this invention.

FIG. 11 illustrates an alternative embodiment of this invention.

FIG. 12 is a cross-sectional view of a filter punch of this invention having a depressed guide means.

FIG. 13 illustrates an alternative embodiment of this invention.

DESCRIPTION OF SPECIFIC EMBODIMENTS

Figure 1:
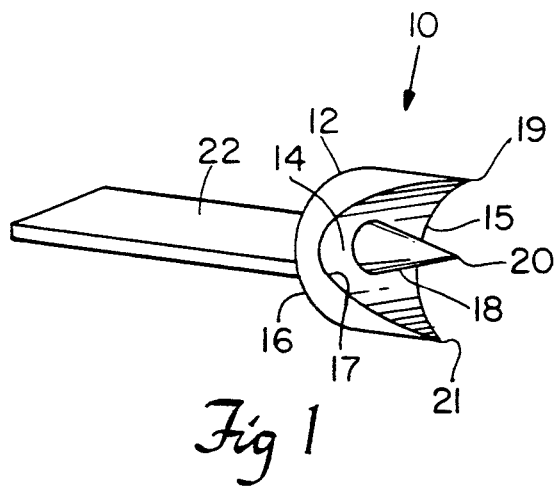
FIG. 1 shows a filter punch of this invention.
Figure 4:
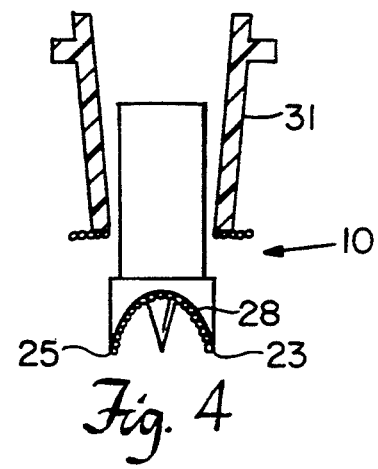
FIG. 4 illustrates the second step of the use of the filter punch of this invention.

Referring to FIG. 1 and 4, the filter punch 10 includes a punch section 12 having a flat following surface 16. A single angle conically shaped piercing member 18 is secured to a central portion of curved surface 14. The edges 15 and 17 comprise cutting edges for cutting the periphery of a membrane filter secured to a well. The conically shaped piercing member 18 has a sharp point 20 adapted to pierce a filter membrane. On the surface 16 a die-punch guide 22 is secured which functions to position a hollow die (not shown) about the circumference of punch section 12 so that even distribution of force across the punch section 12 can be applied. The guide member 22 can be of any shape such as shown in FIG. 1, cylindrical, hollow cylindrical or cruciform. The sides of the filter piercing member 18 form an angle with the vertical axis of the piercing member of between about 2° and about 45°, preferably between about 5° and about 30° and have a length generally between about 0.2 mm and about 10 mm, preferably between about 1 mm and about 3 mm. The peripheral points can have a length generally between about 0.1 mm and about 10 mm, preferably between about 0.2 mm and about 4 mm.

Figure 2:
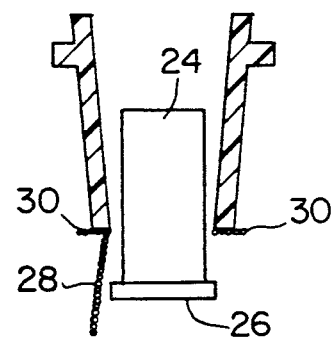
FIG. 2 illustrates the undesirable operation of one embodiment of the prior art.

Referring to FIG. 2, the filter punch 24 of the prior art has a flat face 26 which is designed to sever filter section 28 from the remaining portion of the filter 30 so that it will be directed to a receptacle (not shown). However, the flat face 26 frequently causes incomplete severance so that the filter section 28 remains hinged on to filter section 30 rather than dropping into the desired receptacle.

Figure 3:
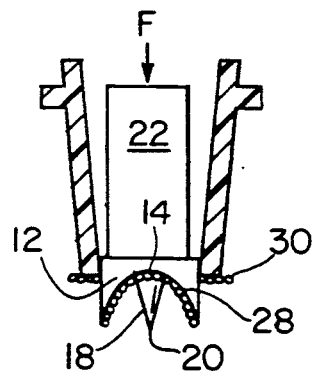
FIG. 3 illustrates the first step of the use of the filter punch of this invention.

Referring to FIGS. 1 and 3, the filter punch of this invention is utilized so that a force (F) is applied directly or indirectly to punch section 12 so that point 20 of conically shaped piercing member 18 penetrates filter 28 at substantially the same time as edges 15 and 17 or at least before the entire surface 14 has contacted the filter. The peripheral points 23 and 25 substantially prevent slippage of the membrane across the surface 14 thereby to prevent the undesirable result of having the filter section hinge as shown in FIG. 2. As shown on FIG. 4, the filter punch 10 and filter section 28 are passed from well 31 into a receptacle (not shown).

Figure 5:
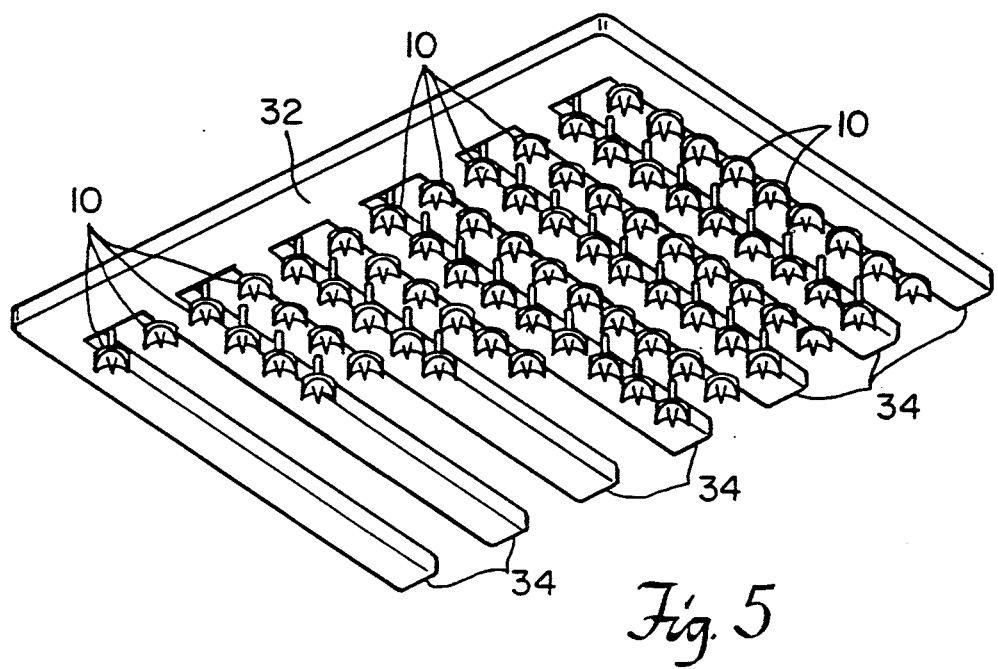
FIG. 5 illustrates the filter punch holder of this invention.

Referring to FIG. 5, a filter punch holder of this invention is shown which includes a base member 32 and a plurality of arms 34 which are attached to the base member 32 and extend substantially parallel to each other. A plurality of filter punches 10 as shown in FIG. 1 are secured along the length of each of the arms 34 substantially equidistant from each other as shown in FIG. 5. The distance between the punches 10 is such as to accommodate the distance between the wells 36 in the multiwell filtration apparatus (FIG. 6). The punches 10 can be secured to the arms 34 by any means. However, it is preferred that the base 32, arms 34 and filter punches 10 be molded as one piece in order to facilitate placement of as many as 96 punches 10 over the corresponding wells 36. It is also preferable to secure each punch 10 to the arms 34 in at least two places to maintain alignment and relative position of each punch 10. The filter punch holder shown in FIG. 5 is utilized in conjunction with multiple plungers which are positioned to parallel the rows of filter punches 10 shown in FIG. 5. The filter punches 10 are positioned above wells 36 ad pass through the filter in the manner shown in FIGS. 3 and 4 to sever the filter from the wells 36 whereby individual filter punches 10 and filter sections 28 pass into vials 38 by means of chutes 40. Each punch 10 adds enough mass to each filter section 28 to cause the combination to slide down a chute 40 while the filter section 28 alone would adhere to the chute 40.

The filter punch construction of this invention as exemplified by FIGS. 1, 7, 8, 9, 10 and 11 is made so that the centrally located piercing member, during use stabilizes the filter during punching so that it is severed about its entire periphery. The piercing member provides an anchor point to hold the punched filter and has a point which is sufficiently sharp to pierce the filter 30 at substantially the same time as the edges 15 and 17 pierce the filter 30. The sides of the piercing member should form a small angle with its vertical side so that the piercing member can penetrate the filter easily. By forming the sides of the piercing member so that they form a small angle with the vertical axis, the pierced filter will more easily grip the piercing member. As shown in FIG. 7, the piercing member 42 can be formed as a double cone and the cutting edges 41 and 43 converge to a sharp point 45. The cutting edges 41 and 43 intersect each other to assure complete cutting of the membrane by the cutting edges 41 and 43. The piercing member 44 shown in FIG. 8 is in the form of a pyramid. The piercing member 46 shown in FIG. 9 has a cruciform shape. The piercing member 48 shown in FIG. 10 has a stiletto shape. The piercing member 50 shown in FIG. 11 has an undercut 52 so that it functions as a barb. As shown in FIG. 11, the undercut 52 has a smaller cross section then the base of piercing member 50.

As shown in FIG. 12 the guide member 54 is in the form of a conical depression which mates with a punch (not shown) to stabilize and effect the desired force on the punch 56 having piercing member 58 of this invention. The punch 56 can be attached to the base member 32 (FIG. 5) at surface 53 or surface 55 to permit a punch (not shown) to mate with guide member 54. Thus, the guide member utilized in the present invention may either be an extension or depression relative to the punch section.

As shown in FIG. 13, a plurality of peripheral points 58 which are shorter than the central point 60 are provided. The peripheral points 58 substantially prevent slippage of a pierced membrane across surface 59. It is not necessary that the peripheral points 58 intersect each other. They can by separated by flat surfaces if desired.

The peripheral points shown in FIG. 1, the centrally located piercing member of FIG. 7 and the cylindrical guide member shown in FIG. 11, in combination comprise a preferred embodiment of this invention. Although several embodiments of the invention have been described in detail above, modifications will become apparent to those of skill in the art. All that is required is that a central piercing point be provided and a plurality of peripheral piercing points be provided.

Accordingly, the invention is intended to be limited only by the appended claims.

We claim:

1. A filter punch which comprises a punch section having a thickness and two opposing surfaces,
   a filter piercing member secured to and extending from a central portion of one of said opposing surfaces, said one of said opposing surfaces having a plurality of peripheral piercing points extending substantially in the same direction as said filter piercing member, said filter piercing member having a sharp point and having a side area and a vertical axis, said side area and said vertical axis forming a small angle such that a filter pierced by said piercing member is secured to said piercing member and
   a punch guide formed on the second of said opposing surfaces, said punch section, piercing member and punch guide having a size and shape to permit said filter punch to pass through a filter having substantially the same size and shape of said one of said opposing surfaces.

2. The filter punch of claim 1 wherein said filter piercing member is conically shaped.

3. The filter punch of any one of claims 1 or 2 wherein said piercing member has a conical angle between about 5° or 30°.

4. The filter punch of claim 1 wherein said filter piercing member is secured to one of said opposing surfaces by means of a cylindrical member.

5. The filter punch of claim 4 wherein said cylindrical member has a cross-section smaller than a base of said filter piercing member.

6. The filter punch of claim 1 wherein said punch is used to convey said filter to receiving means.

7. A filter punch holder which comprises; a base member,
   a plurality of arms attached to said base member, said arms being positioned substantially parallel to each other,
   each of said arms having a plurality of filter punches secured along the length of said arms, said filter punches being positioned substantially equidistant from each other,
   each of said filter punches comprising a punch section having a thickness, two opposing surfaces and a filter piercing member secured to and from a central portion of one of said opposing surfaces, said one of said opposing surfaces having a plurality of peripheral piercing points extending substantially in the same direction as said filter piercing member, said filter piercing member having a sharp point and having a side area and a vertical axis, said side are and said vertical axis forming a small angle such that a filter pierced by said piercing member is secured to said piercing member
   and a punch guide on the second of said opposing surfaces,
   said punch section, piercing member and punch guide having a size and shape to permit said filter punches to pass through a filter having substantially the same size and shape of said one of said opposing surfaces.

8. The filter punch holder of claim 7 which is formed of unitary construction.

9. The filter punch holder of claim 7 wherein said filter piercing member is conically shaped.

10. The filter punch holder of any one of claims 7, 8 or 9 wherein said piercing member has a conical angle between about 5° and 30°.

11. The filter punch of any one of claims 1, 2, 7, 8 or 9 wherein said plurality of piercing points comprises a smooth curved surface extending from said punch section.

* * * * *